(12) United States Patent
Audousset et al.

(10) Patent No.: US 7,811,336 B2
(45) Date of Patent: Oct. 12, 2010

(54) COMPOSITIONS COMPRISING AT LEAST ONE AMINATED SILICONE AND MONOETHANOLAMINE, AND METHODS AND DEVICES FOR USE THEREOF

(75) Inventors: Marie-Pascale Audousset, Asnieres (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/149,704

(22) Filed: May 7, 2008

(65) Prior Publication Data
US 2008/0282482 A1 Nov. 20, 2008

Related U.S. Application Data

(60) Provisional application No. 60/924,805, filed on May 31, 2007.

(30) Foreign Application Priority Data
May 7, 2007 (FR) ................................. 07 54911

(51) Int. Cl.
*A61Q 5/10* (2006.01)
(52) U.S. Cl. .................. 8/405; 8/406; 8/410; 8/435; 8/552; 8/554
(58) Field of Classification Search ............ 8/405, 8/406, 410, 435, 552, 554
See application file for complete search history.

(56) References Cited

U.S. PATENT DOCUMENTS

| | | | |
|---|---|---|---|
| 5,628,799 | A | 5/1997 | Wenke et al. |
| 6,156,076 | A | 12/2000 | Casperson et al. |
| 6,475,248 | B2 | 11/2002 | Ohashi et al. |
| 7,101,405 | B2 | 9/2006 | Cottard et al. |
| 2001/0023514 | A1 | 9/2001 | Cottard et al. |
| 2001/0023515 | A1 | 9/2001 | Cottard et al. |
| 2002/0046431 | A1 | 4/2002 | Laurent et al. |
| 2002/0189034 | A1* | 12/2002 | Kitabata et al. ............ 8/405 |
| 2003/0140429 | A1 | 7/2003 | Legrand et al. |
| 2004/0163187 | A1* | 8/2004 | Cottard et al. ............ 8/405 |
| 2008/0276385 | A1 | 11/2008 | Cottard et al. |

FOREIGN PATENT DOCUMENTS

| | | |
|---|---|---|
| EP | 0 497 163 | 8/1992 |
| EP | 0 890 355 | 1/1999 |
| EP | 1 426 038 | 6/2004 |
| EP | 1 803 434 | 7/2007 |
| FR | 2 831 807 | 5/2003 |
| WO | WO 00/07550 | 2/2000 |
| WO | WO 00/56285 | 9/2000 |
| WO | WO 01/72271 | 10/2001 |
| WO | WO 02/38116 | 5/2002 |
| WO | WO 02/47632 | 6/2002 |
| WO | WO 02/074273 | 9/2002 |
| WO | WO 02/078661 | 10/2002 |

OTHER PUBLICATIONS

STIC Search Report dated Apr. 14, 2009.*
37 C.F.R. § 1.132 Declaration filed Jun. 27, 2007, in U.S. Appl. No. 10/728,954 (parent of Copending U.S. Appl. No. 12/168,270, filed Jul. 7, 2008), signed by Marie-Pascale Audousset.
37 C.F.R. § 1.132 Declaration filed Nov. 30, 2007, in U.S. Appl. No. 10/728,954 (parent of Copending U.S. Appl. No. 12/168,270, filed Jul. 7, 2008), signed by Isabelle Schlosser.
Copending U.S. Appl. No. 12/168,270, filed Jul. 7, 2008.
European Search Report for EP 08 15 5494, dated Aug. 28, 2008.
French Search Report for FR 02/15470, dated Jun. 27, 2003.
French Search Report for FR 07/54911, dated Jan. 7, 2008.
Office Action mailed May 11, 2009, in co-pending U.S. Appl. No. 12/168,270.
Office Action mailed Sep. 12, 2008, in co-pending U.S. Appl. No. 12/168,270.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to compositions for dyeing keratinous fibers, for example human keratinous fibers, such as hair, wherein the compositions comprise, in a medium appropriate for dyeing, at least one oxidation base, at least one coupler, at least one aminated silicone, and monoethanolamine, wherein the at least one aminated silicone has a weight-average molecular weight ($M_w$) of greater than or equal to 75,000 g/mol, and monoethanolamine is present in an amount ranging from 1 to 10% by weight relative to the total weight of the composition. The present disclosure also relates to methods of dyeing keratinous fibers using said compositions and devices comprising the compositions.

27 Claims, No Drawings

COMPOSITIONS COMPRISING AT LEAST ONE AMINATED SILICONE AND MONOETHANOLAMINE, AND METHODS AND DEVICES FOR USE THEREOF

This application claims benefit of U.S. Provisional Application No. 60/924,805, filed May 31, 2007, the contents of which are incorporated herein by reference. This application also claims benefit of priority under 35 U.S.C. §119 to French Patent Application No. FR 0754911, filed May 7, 2007, the contents of which are also incorporated herein by reference.

The present disclosure relates to compositions for dyeing keratinous fibers, for example human keratinous fibers such as the hair, wherein the compositions comprise at least one oxidation base, at least one coupler, at least one specific aminated silicone, and monoethanolamine. The disclosure also relates to methods for dyeing keratinous fibers using such compositions and to devices comprising such compositions.

It is known to dye keratinous fibers, for example human keratinous fibers such as the hair, with dyeing compositions comprising oxidation dye precursors, which may be known as oxidation bases, such as ortho- and para-phenylenediamines, ortho- and para-aminophenols, and heterocyclic bases. Oxidation dye precursors and oxidation bases are initially colorless or weakly colored compounds which, in combination with oxidizing agents, can give rise, by an oxidative coupling process, to colored and coloring compounds.

It is also known to vary the shades obtained with these oxidation bases by combining them with couplers and/or coloring modifiers, the latter being chosen for example from meta-diaminobenzenes, meta-aminophenols, meta-diphenols, and certain heterocyclic compounds, such as indole compounds.

The variety of compounds which may be used as oxidation bases and couplers makes it possible to obtain a rich palette of colors.

However, conventional oxidation colorings may result in inconveniences and/or discomfort during application, such as redness or smarting of the skin, for example the scalp.

It is thus desirable to find dyeing compositions which make it possible to minimize irritation of the scalp, in order to render the application of these compositions more comfortable for the user while resulting in satisfactory coloring.

The present inventors have discovered, surprisingly, that it is possible to obtain novel dyeing compositions which can reduce the discomfort and/or side effects which may be felt during the application of the dyeing compositions, such as the appearance of redness and/or smarting on the scalp, while resulting in powerful, chromatic, and not very selective coloring which are highly resistant to the various attacks to which the hair may be subjected.

Thus, disclosed herein are compositions for dyeing keratinous fibers, for example human keratinous fibers such as the hair, wherein the composition comprises at least one oxidation base, at least one coupler, monoethanolamine, wherein the monoethanolamine is present in an amount ranging from 1 to 10% by weight relative to the total weight of the composition, and at least one aminated silicone with a weight-average molecular weight of greater than 75,000 g/mol.

Also disclosed herein is a method for dyeing human keratinous fibers, for example the hair, which comprises applying, to the fibers, a composition according to the present disclosure.

Also disclosed herein is a multicompartment kit or dyeing device comprising a at least one first compartment, wherein said first compartment comprises a composition comprising, in a medium appropriate for dyeing, at least one oxidation base, at least one coupler, at least one aminated silicone with a weight-average molecular weight of greater than or equal to 75,000 g/mol, and monoethanolamine, wherein the monoethanolamine is present in an amount ranging from 1 to 10% by weight, relative to the total weight of the composition, and at least one second compartment, wherein said second compartment comprises a composition comprising, in a medium appropriate for dyeing, at least one oxidizing agent.

The various embodiments of the present disclosure are described in more detail below. All meanings and definitions provided herein with respect to the compounds used in the present disclosure are applicable to all embodiments of the present disclosure.

As used herein, the limits delimiting a range of values are included in this range, unless otherwise indicated.

As used herein, "oxidizing agent" is understood to mean any compound, other than atmospheric oxygen, having oxidizing properties.

According to one aspect of the present disclosure, the dyeing compositions in accordance with the present disclosure can make it possible to minimize the discomfort which may be felt during the application of the dyeing compositions.

According to another aspect of the present disclosure, dyeing compositions in accordance with the present disclosure can also result in powerful and chromatic colorings, which can exhibit a low selectivity and excellent properties of resistance, for example with regard to shampoos.

The at least one aminated silicone used in compositions in accordance with the present disclosure are chosen from those of formula (I):

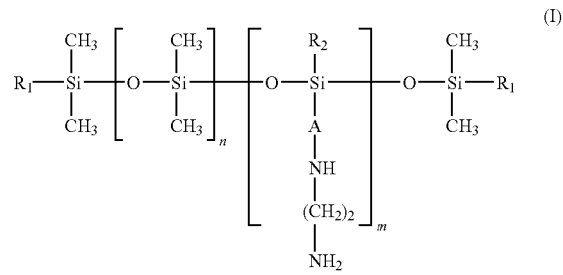

wherein:
A is chosen from linear and branched $C_2$-$C_8$ alkylene radicals, for example $C_3$ alkylene radicals,
$R_1$ and $R_2$ are, independently of one another, chosen from $C_1$-$C_4$ alkyl radicals, for example methyl radicals, $C_1$-$C_4$ alkoxy radicals, for example methoxy radicals, and hydroxyl radicals,
m and n are numbers such that the weight-average molecular weight ($M_w$) of the at least one aminated silicone is greater than or equal to 75,000 g/mol.

According to the present disclosure, the viscosity of the at least one aminated silicone can be, for example, greater than 25,000 mm$^2$/s measured at 25° C. In at least one embodiment of the present disclosure, the viscosity of the at least one aminated silicone ranges from 30,000 to 200,000 mm$^2$/s at 25° C., for example, from 30,000 to 150,000 mm$^2$/s, measured at 25° C. The viscosities of the silicones are, for example, measured according to Standard "ASTM 445 Appendix C."

In at least one embodiment of the present disclosure, the cationic charge of the at least one aminated silicone is less than or equal to 0.06 meq/g.

In at least one embodiment of the present disclosure, the weight-average molecular weight ($M_w$) of the at least one aminated silicone ranges from 75,000 to 1,000,000 g/mol, for example, from 100,000 to 200,000 g/mol.

The weight-average molecular weight of the silicones may be measured by gel permeation chromatography (GPC) at ambient temperature using polystyrene equivalents. For example, μ-styragel columns may be used with THF as the eluent and a flow rate of 1 ml/min. For example, 200 μl of a 0.5% by weight solution of silicone in THF may be injected. Detection may be carried out by refractometry and ultraviolet spectroscopy.

In at least one embodiment, the at least one aminated silicone according to the present disclosure may be used in the form of an oil-in-water emulsion. The oil-in-water emulsion can comprise at least one surfactant, which may be of any nature. For example, the surfactants may be cationic or nonionic.

In at least one embodiment, the silicone particles in the oil-in-water emulsion may have a mean size ranging from 3 nm to 500 nm, for example from 5 nm to 300 nm, for example from 10 nm to 275 nm, and for example from 150 nm to 275 nm.

A non-limiting example of the at least one aminated silicone, includes DC2-8299® from Dow Corning.

The at least one aminated silicone is present in dyeing compositions according to the present disclosure in an amount ranging from 0.01 to 20% by weight, for example from 0.1 to 15% by weight, and for example from 0.5 to 10% by weight, relative to the total weight of the composition.

The at least one oxidation base which can be used in compositions according to the present disclosure may be chosen from those conventionally known in oxidation dyeing. Non-limiting examples of the oxidation base include ortho- and para-phenylenediamines, double bases, ortho- and para-aminophenols, and the heterocyclic bases described below, as well as the acid addition salts thereof.

As used herein, "double bases" is understood to refer to compounds comprising at least two aromatic nuclei on which are carried amino and/or hydroxyl groups.

Non-limiting examples of oxidation bases which may be used in compositions according to the present disclosure include:

(A) Para-phenylenediamines chosen from those of formula (II) and the acid addition salts thereof:

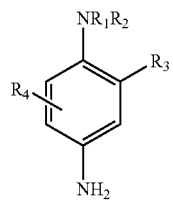

wherein:
$R_1$ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy-($C_1$-$C_4$)alkyl radicals, $C_1$-$C_4$ alkyl radicals substituted by a nitrogenous group, phenyl radicals, and 4'-aminophenyl radicals;
$R_2$ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy-($C_1$-$C_4$)alkyl radicals, and $C_1$-$C_4$ alkyl radicals substituted by a nitrogenous group;
$R_1$ and $R_2$ may also form, with the nitrogen atom which carries them, a 5- or 6-membered nitrogenous heterocycle, optionally substituted with at least one group chosen from alkyl, hydroxyl, and ureido groups;
$R_3$ is chosen from a hydrogen atom, a halogen atom, for example a chlorine atom, $C_1$-$C_4$ alkyl radicals, sulfo radicals, carboxyl radicals, $C_1$-$C_4$ monohydroxyalkyl radicals, $C_1$-$C_4$ hydroxyalkoxy radicals, $C_1$-$C_4$ acetylaminoalkoxy radicals, $C_1$-$C_4$ mesylaminoalkoxy radicals, and $C_1$-$C_4$ carbamoylaminoalkoxy radicals;
$R_4$ is chosen from a hydrogen atom, a halogen atom, and $C_1$-$C_4$ alkyl radicals.

As nitrogenous groups of the above formula (II), non-limiting examples include amino, mono($C_1$-$C_4$)alkylamino, di($C_1$-$C_4$)alkylamino, tri($C_1$-$C_4$)alkylammonium, monohydroxy($C_1$-$C_4$)alkylamino, imidazolinium, and ammonium radicals.

As para-phenylenediamines of the above formula (II), non-limiting examples include para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-[N,N-bis(β-hydroxyethyl)amino]-2-methylaniline, 4-[N,N-bis(β-hydroxyethyl)amino]-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine, and their addition salts with an acid.

In another embodiment of the present disclosure, as para-phenylenediamines of the above formula (II), non-limiting examples include para-phenylenediamine, para-toluoylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and their addition salts with an acid.

(B) Double bases of formula (III) and the acid addition salts thereof:

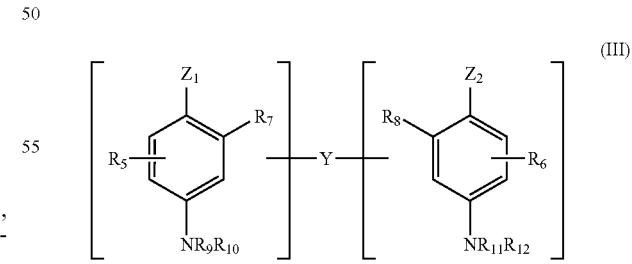

wherein:
$Z_1$ and $Z_2$, are, independently of one another, chosen from hydroxyl and —$NH_2$ radicals, which may be substituted by $C_1$-$C_4$ alkyl radicals or by a connecting arm Y;
the connecting arm Y is chosen from divalent linear and branched $C_1$-$C_{14}$ alkylene radicals, which may be interrupted or terminated by at least one group chosen from nitrogenous groups and heteroatoms, for example oxygen, sulfur, and nitrogen atoms, and which may be substituted by at least one radical chosen from hydroxyl and $C_1$-$C_6$ alkoxy radicals;

$R_5$ and $R_6$, are, independently of one another, chosen from a hydrogen atom, a halogen atom, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and a connecting arm Y;

$R_7$, $R_8$, $R_9$, $R_{10}$, $R_{11}$, and $R_{12}$, are, independently of one another, chosen from a hydrogen atom, a connecting arm Y, and $C_1$-$C_4$ alkyl radicals;

it being understood that the compounds of formula (III) comprise a single connecting arm Y per molecule.

As nitrogenous groups of the above formula (III), non-limiting examples include amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium, and ammonium radicals.

As double bases of the above formula (III), non-limiting examples include N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)-tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diaminophenoxy)-3,6-dioxaoctane, and their addition salts with an acid.

In at least one embodiment of the present disclosure, non-limiting examples of the double bases of formula (III) include N,N'-bis(β-hydroxyethyl)-N,N'-bis(4'-aminophenyl)-1,3-diaminopropanol, 1,8-bis(2,5-diaminophenoxy)-3,6-dioxaoctane, and addition salts with an acid.

(C) Para-aminophenols of formula (IV) and their addition salts with an acid:

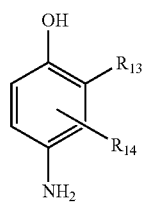

(IV)

wherein:

$R_{13}$ is chosen from a hydrogen atom, a halogen atom, for example a fluorine atom, $C_1$-$C_4$ alkyl radicals, $C_1$-$C_4$ monohydroxyalkyl radicals, ($C_1$-$C_4$)alkoxy-($C_1$-$C_4$) alkyl radicals, $C_1$-$C_4$ aminoalkyl radicals, and hydroxy ($C_1$-$C_4$)-alkylamino($C_1$-$C_4$)alkyl radicals, $R_{14}$ is chosen from a hydrogen atom, a halogen atom, for example a fluorine atom, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, $C_1$-$C_4$ cyanoalkyl radicals, and ($C_1$-$C_4$)alkoxy-($C_1$-$C_4$)alkyl radicals.

As para-aminophenols of formula (IV), non-limiting examples include para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, and the acid addition salts thereof.

(D) Ortho-aminophenols. As ortho-aminophenols which may be used as oxidation bases in compositions according to the present disclosure, non-limiting mention may be made of 2-aminophenol, 2-amino-1-hydroxy-5-methylbenzene, 2-amino-1-hydroxy-6-methylbenzene, 5-acetamido-2-aminophenol, and the acid addition salts thereof.

(E) Heterocyclic bases. As heterocyclic bases which may be used as oxidation bases in compositions according to the present disclosure, non-limiting examples include pyridine derivatives, pyrimidine derivatives, pyrazole derivatives, and the acid addition salts thereof.

As pyridine derivatives which may be used in compositions according to the present disclosure, non-limiting examples include the compounds disclosed in Patents GB 1 026 978 and GB 1 153 196, for example 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

As pyrimidine derivatives which may be used in compositions according to the present disclosure, non-limiting examples include the compounds disclosed in German Patent DE 2 359 399, Japanese Patents JP 88-169 571 and JP 91-10659, and PCT Publication WO 96/15765, for example 2,4,5,6-tetraminopyrimidine, 4-hydroxy-2,5,6-triaminopyrimidine, 2-hydroxy-4,5,6-triaminopyrimidine, 2,4-dihydroxy-5,6-diamino-pyrimidine, 2,5,6-triaminopyrimidine, and pyrazolopyrimidine derivatives, and those mentioned in French Patent Application FR 2 750 048, for example pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidine-5-ol; 2-(3-amino-pyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and their tautomeric forms, when a tautomeric equilibrium exists, and the acid addition salts thereof.

As pyrazole derivatives which may be used in compositions according to the present disclosure, additional non-limiting examples include the compounds disclosed in German Patents DE 3 843 892 and DE 4 133 957, PCT Publications WO 94/08969 and WO 94/08970, French Patent Application FR 2 733 749, and German Patent Application DE 195 43 988, for example 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methyl-pyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5- triaminopyrazole, 3,5-diamino-1-methyl-4-(methylamino)pyrazole, 3,5-diamino-4-(β-hydroxyethyl)amino-1-methylpyrazole, and the acid addition salts thereof.

As couplers which may be used in the ready-for-use dyeing compositions according to the present disclosure, non-limiting examples include those conventionally used in oxidation dyeing compositions, for example meta-aminophenols, meta-phenylenediamines, meta-diphenols, naphthols, and heterocyclic couplers, such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and the acid addition salts thereof.

In at least one embodiment of the present disclosure, non-limiting examples from which the couplers may be chosen include 2,4-diamino-1-(β-hydroxyethyloxy)benzene, 2-methyl-5-aminophenol, 5-[N-(β-hydroxyethyl)amino]-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methyl-pyrazol-5-one, 1-phenyl-3-methylpyrazol-5-one, 2-amino-3-hydroxypyridine, 3,6-dimethylpyrazolo[3,2-c][1,2,4]triazole, 2,6-dimethylpyrazolo-[1,5-b][1,2,4]triazole, and the acid addition salts thereof.

The at least one oxidation base and the at least one coupler may be present in an amount ranging from 0.0005 to 12% by weight, for example from 0.01 to 8% by weight, relative to the total weight of the composition.

In at least one embodiment of the present disclosure, non limiting examples from which the acid addition salts of the oxidation bases and couplers may be chosen include hydrochlorides, hydrobromides, sulfates, tartrates, lactates, and acetates.

In at least one embodiment, compositions according to the present disclosure may further comprise sodium metasilicate. In at least one embodiment, sodium metasilicate may be present in compositions according to the present disclosure in an amount ranging from 0.1 to 10% by weight, for example from 0.5 to 5% by weight, for example from 1 to 4% by weight, relative to the total weight of said compositions.

The dyeing compositions according to the present disclosure may further comprise at least one adjuvant conventionally used in hair dyeing compositions, such as anionic, cationic, nonionic, amphoteric, and zwitterionic surface-active agents and their mixtures, anionic, cationic, nonionic, amphoteric, and zwitterionic polymers and their blends, inorganic and organic thickening agents, for example anionic, cationic, nonionic, and amphoteric polymeric associative thickeners, antioxidants, penetration agents, sequestering agents, fragrances, buffers, dispersing agents, conditioning agents, such as, for example, volatile and nonvolatile and modified and unmodified silicones, film-forming agents, ceramides, preservatives, and opacifying agents.

The at least one of the above adjuvants may be present in compositions according to the present disclosure in an amount ranging from 0.01 to 20% by weight, relative to the total weight of the composition.

A person skilled in the art will take care to choose the optional additional compound or compounds mentioned above so that the beneficial properties of dyeing compositions according to the present disclosure are not, or not substantially, detrimentally affected by the envisaged addition or additions.

The medium appropriate for dyeing for the ready-for-use dyeing compositions according to the present disclosure may be an aqueous medium comprising water and may optionally further comprise at least one organic solvent which is cosmetically acceptable; non-limiting examples include alcohols, such as ethyl alcohol, isopropyl alcohol, benzyl alcohol, and phenylethyl alcohol, glycols and glycol ethers, such as ethylene glycol monomethyl, monoethyl and monobutyl ethers, propylene glycol and its ethers, such as propylene glycol monomethyl ether, butylene glycol, dipropylene glycol and diethylene glycol, and alkyl ethers, such as diethylene glycol monoethyl ether and monobutyl ether. The optional organic solvents may be present in amounts ranging from 0.5 to 20% by weight, for example from 2 to 10% by weight, relative to the total weight of the composition.

The compositions according to the present disclosure can have a pH ranging from 3 to 12, for example from 7 to 11. The pH of compositions according to the present disclosure may be adjusted to a particular value by addition of acidifying or basifying agents, for example those known by one of skill in the art in dyeing keratinous fibers.

As basifying agents, a non-limiting example includes monoethanolamine, which may be used alone or in combination with other basifying agents. In one embodiment, compositions according to the present disclosure comprise only monoethanolamine as basifying agent.

Non-limiting examples of acidifying agents include inorganic and organic acids, such as hydrochloric acid, orthophosphoric acid, carboxylic acids, such as tartaric acid, citric acid, and lactic acid, and sulfonic acids.

The present disclosure also relates to methods for dyeing keratinous fibers, for example human keratinous fibers such as the hair, comprising applying to the fibers a composition according to the present disclosure in the presence of an oxidizing agent for a time sufficient to develop the desired coloring effect.

In at least one embodiment of methods according to the present disclosure, at least one composition according to the present disclosure is applied to the fibers for a time sufficient to develop the desired coloring, after which the fibers are rinsed, optionally washed with shampoo, rinsed again, and dried.

In one embodiment, the oxidizing agent can be added to the composition according to the present disclosure directly on the keratinous fibers, before or after application of the composition of the present disclosure. In another embodiment, the oxidizing agent is added to the composition according to the present disclosure at the time of use. In one embodiment, the resulting mixture is subsequently applied to the keratinous fibers. After a setting time ranging from 3 to 50 minutes, for example from 5 to 30 minutes, the keratinous fibers are rinsed, washed with shampoo, rinsed again, and then dried.

As oxidizing agents which may be used for the oxidation dyeing of keratinous fibers, non-limiting examples include hydrogen peroxide, urea hydrogen peroxide, alkali metal bromates, persalts, such as perborates and persulfates, peracids, and oxidase enzymes, such as peroxidases, 2-electron oxidoreductases, such as uricases, and 4-electron oxygenases, such as laccases. In one embodiment, hydrogen peroxide may be used.

The oxidizing compositions according to the present disclosure may also include at least one adjuvant, for example adjuvants chosen from those conventionally used in hair dyeing compositions and as defined above.

In one embodiment, monoethanolamine is present in compositions according to the present disclosure, after mixing with the oxidizing agent, in an amount ranging from 0.5 to 10% by weight, for example from 1 to 5% by weight, relative to the total weight of the composition resulting from the mixing.

The present disclosure also relates to the use of compositions according to the present disclosure for dyeing keratinous fibers, for example human keratinous fibers such as the hair.

The present disclosure also relates to multicompartment devices and kits for dyeing, and any other multicompartment packaging system, wherein at least one first compartment comprises a composition according to the present disclosure and wherein at least one second compartment comprises a composition comprising at least one oxidizing agent.

In one embodiment, devices according to the present disclosure may be equipped with an applicator allowing the desired mixture to be delivered to the hair, for example the application devices described in French Patent No. FR 2 856 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES

Example I

Two compositions in accordance with the present disclosure were prepared from the following compounds:

(quantities expressed as grams, unless otherwise indicated)

|  | Composition 1 | Composition 2 |
| --- | --- | --- |
| 1-Methyl-2,5-diaminobenzene | 1.7 | 0.5 |
| 1-Hydroxy-4-aminobenzene |  | 0.4 |
| 1,3-Dihydroxybenzene | 1 | 0.25 |
| 1-Hydroxy-3-aminobenzene | 0.07 |  |
| 1-(β-Hydroxyethyloxy-2,4-diamino)benzene dihydrochloride | 0.03 |  |
| 2-Methyl-1,3-dihydroxybenzene | 0.5 | 0.3 |
| 1-Methyl-2-hydroxy-4-aminobenzene |  | 0.25 |
| 1-Methyl-2-hydroxy-4-(β-hydroxyethylamino)benzene |  | 0.05 |
| 6-Hydroxyindole |  | 0.01 |
| Anhydrous sodium metasilicate |  | 2 |

-continued

|  | Composition 1 | Composition 2 |
| --- | --- | --- |
| Pure monoethanolamine | 5 | 10 |
| Polyquaternium 6 (sold under the name Merquat 100 by Ondeo) |  | 3 |
| Polyquaternium 22 (sold under the name Merquat 280 by Ondeo) | 1.5 |  |
| Hexadimethrine chloride (sold under the name Mexomere PO by Chimex) | 1.5 |  |
| Propylene glycol | 10 | 10 |
| Crosslinked polyacrylic acid | 0.4 | 0.4 |
| Oxyethylenated lauryl alcohol (12 EO) | 7.5 | 7.5 |
| Oxyethylenated oleocetyl alcohol (30 EO) | 6 | 6 |
| Oxyethylenated decyl alcohol (3 EO) | 8 | 8 |
| Lauric acid | 2.5 | 2.5 |
| 50/50 Cetearyl alcohol | 10 | 10 |
| Pyrogenic silica | 1 | 1 |
| DC2-8299 ® from Dow Corning (aminated silicone according to the present disclosure) | 3% AM | 1% AM |
| Glycerol monostearate | 1 | 1 |
| Reducing agent, sequestering agent, antioxidant, fragrance | q.s. | q.s. |
| Demineralized water q.s. | 100 | 100 |

One part of Composition 1 was mixed with one and a half parts aqueous hydrogen peroxide solution. One part of Composition 2 was mixed with one and a half parts aqueous hydrogen peroxide solution. In resulting Composition 1, the hydrogen peroxide used was at 2.7% by weight, relative to the total weight of the composition. In resulting Composition 2, the hydrogen peroxide used was at 6% by weight, relative to the total weight of the composition. The pH of the aqueous hydrogen peroxide compositions was about 2.3.

Two ready-for-use dyeing compositions were thus obtained.

The concentration of monoethanolamine in the ready-for-use dyeing Compositions 1 and 2 was 2.5% by weight and 4% by weight respectively, relative to the total weight of the ready-for-use compositions.

The ready-for-use dyeing Composition 1 had a pH of 9.8 and the ready-for-use dyeing Composition 2 had a pH of 10.

After preparation, the two ready-for-use dyeing compositions were applied to grey hair comprising 90% white hairs. The leave-on time was 20 minutes. The hair was subsequently washed with a standard shampoo, then rinsed with water and dried.

The coloring of the hair was evaluated visually.

It should be remembered that the notion of "tone" is based on the classification of natural shades, one tone separating each shade from that which immediately follows or precedes it. This definition and the classification of natural shades are known to professionals in hairstyling and are discussed, for example, in the work "The Science of Hair Care" by Charles Zviak 1988, published by Masson, pp. 215 and 278.

| 90% Natural white hairs | Height of tone | Highlight |
| --- | --- | --- |
| Ready-for-use dyeing Composition 1 | Chestnut | Natural |
| Ready-for-use dyeing Composition 2 | Dark blond | Coppery mahogany |

Discomfort related to the application to the hair of the ready-for-use dyeing Compositions 1 and 2 was not observed.

In particular, it was noticed that the application of these two compositions did not result in irritation of the scalp.

In addition, these dyeing compositions made it possible to obtain colorings which were powerful, chromatic, and not very selective, and which were highly resistant to shampoos.

Example II

A composition (A) in accordance with the present disclosure and a comparative composition (B) not comprising at least one aminated silicone were prepared from the compounds shown in Table II:

(quantities expressed as grams, unless otherwise indicated)

TABLE II

|  | A (inventive) | B (comparative) |
|---|---|---|
| DC2-8299 from Dow Corning (aminated silicone according to the present disclosure) | 3 AM | — |
| Lauric acid | 3 | 3 |
| Oxyethylenated lauryl alcohol (12 EO) | 7 | 7 |
| Oxyethylenated decyl alcohol (3 EO) | 10 | 10 |
| 50/50 Cetearyl alcohol | 11.5 | 11.5 |
| Oxyethylenated oleocetyl alcohol (30 EO) | 4 | 4 |
| Tetramethylhexamethylenediamine/1,3-dichloropropylene polycondensate as 60% aqueous solution | 2 | 2 |
| Polydimethyldiallylammonium chloride at 40% in water | 6 | 6 |
| Carboxyvinyl polymer | 0.4 | 0.4 |
| Propylene glycol | 10 | 10 |
| Pure monoethanolamine | 5.45 | 5.45 |
| Pyrogenic silica | 1.2 | 1.2 |
| 1-Methyl-2,5-diaminobenzene | 0.04 | 0.04 |
| 1-Methyl-2-hydroxy-4-(β-hydroxyethylamino)benzene | 0.096 | 0.096 |
| 1,3-Dihydroxybenzene | 0.07 | 0.07 |
| 1-Hydroxy-3-aminobenzene | 0.026 | 0.026 |
| 1-Hydroxy-4-aminobenzene | 0.41 | 0.41 |
| Reducing agent, sequestering agent, antioxidant, fragrance, opacifying agents | q.s. | q.s. |
| Water | q.s. 100 | q.s. 100 |

One part of each of the compositions, (A) and (B), was mixed with one and a half parts of aqueous hydrogen peroxide solution. In the resulting Compositions (A) and (B), the hydrogen peroxide used was at 2.7% by weight, relative to the total weight of the composition. The pH of the resulting ready-for-use dyeing Compositions (A) and (B) was about 2.3.

Ready-for-use dyeing composition (B) and ready-for-use dyeing composition (A) were each applied by way of comparison to 5 models (women aged from 44 to 60 years), having scalps particularly reactive to coloring products. After a leave-in time of 20 minutes and without intermediate rinsing, the hair was rinsed, washed with a standard shampoo, and rinsed again.

When questioned on the intensity of their sensations during the leave-in time, the five models recorded, on a scale from 0 (no sensation of discomfort) to 10 (intolerable discomfort), the discomfort felt on the scalp. The means of the grades reported are shown in Table III:

TABLE III

|  | With ready-for-use dyeing composition (A) | With ready-for-use dyeing composition (B) |
|---|---|---|
| Discomfort | 1.7 | 3.5 |

A 50% reduction in reported discomfort was observed with ready-for-use dyeing composition (A) (comprising an aminated silicone according to the present disclosure) compared to ready-for-use dyeing composition (B) (not comprising an aminated silicone according to the present disclosure).

What is claimed is:

1. A composition for dyeing keratinous fibers comprising, in a medium appropriate for dyeing:
    at least one oxidation base,
    at least one coupler,
    at least one aminated silicone, and
    monoethanolamine,
        wherein the weight-average molecular weight ($M_w$) of the at least one aminated silicone is greater than or equal to 75,000 g/mol, and wherein mixing the composition with a composition comprising at least one oxidizing agent results in a ready-to-use composition containing monoethanolamine in an amount ranging from 1 to 10% by weight, relative to the total weight of the ready-to-use composition.

2. The composition according to claim 1, wherein the at least one aminated silicone is chosen from those of formula (I):

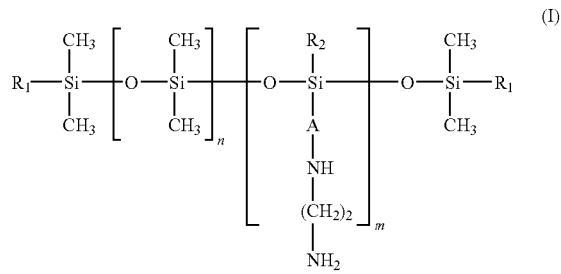

wherein:
    A is chosen from linear and branched $C_2$-$C_8$ alkylene radicals,
    m and n are numbers such that the weight-average molecular weight $M_w$ is greater than or equal to 75,000 g/mol, and
    $R_1$ and $R_2$ are, independently of one another, chosen from $C_1$-$C_4$ alkyl radicals, $C_1$-$C_4$ alkoxy radicals, and hydroxyl radicals,
    and wherein mixing the composition with a composition comprising at least one oxidizing agent results in a ready-to-use composition containing monoethanolamine in an amount ranging from 1 to 5% by weight, relative to the total weight of the ready-to-use composition.

3. The composition according to claim 2, wherein A is chosen from linear and branched $C_3$ alkylene radicals.

4. The composition according to claim 2, wherein $R_1$ and $R_2$ are, independently of one another, chosen from methyl radicals, methoxy radicals, and hydroxyl radicals.

5. The composition according to claim 1, wherein the viscosity of the at least one aminated silicone is greater than 25,000 mm$^2$/s at 25° C.

6. The composition according to claim 5, wherein the viscosity of the at least one aminated silicone ranges from 30,000 to 200,000 mm$^2$/s at 25° C.

7. The composition according to claim 1, wherein the weight-average molecular weight ($M_w$) of the at least one aminated silicone ranges from 100,000 to 200,000 g/mol.

8. The composition according to claim 1, wherein the cationic charge of the at least one aminated silicone is less than or equal to 0.06 meq/g.

9. The composition according to claim 1, wherein the at least one aminated silicone is in the form of an oil-in-water emulsion.

10. The composition according to claim 9, wherein the silicone particles in the oil-in-water emulsion range in size from 3 nm to 500 nm.

11. The composition according to claim 10, wherein the silicone particles in the emulsion range in size from 10 nm to 275 nm.

12. The composition according to claim 1, wherein the at least one aminated silicone is present in an amount ranging from 0.01 to 20% by weight relative to the total weight of the composition.

13. The composition according to claim 12, wherein the at least one aminated silicone is present in an amount ranging from 0.5 to 10% by weight relative to the total weight of the composition.

14. The composition according to claim 1, wherein the at least one oxidation base is chosen from ortho- and para-phenylenediamines, double bases, ortho- and para-aminophenols, heterocyclic bases, and the acid addition salts thereof.

15. The composition according to claim 1, wherein the at least one coupler is chosen from meta-phenylenediamines, meta-aminophenols, meta-diphenols, heterocyclic couplers, and the acid addition salts thereof.

16. The composition according to claim 1, wherein the at least one oxidation base and the at least one coupler are present in an amount ranging from 0.0005 to 12% by weight relative to the total weight of the composition.

17. The composition according to claim 16, wherein the at least one oxidation base and the at least one coupler are present in an amount ranging from 0.01 to 8% by weight relative to the total weight of the composition.

18. The composition according to claim 1, further comprising sodium metasilicate.

19. The composition according to claim 18, wherein the sodium metasilicate is present in an amount ranging from 0.1 to 10% by weight relative to the total weight of the composition.

20. The composition according to claim 19, wherein sodium metasilicate is present in an amount ranging from 1 to 4% by weight relative to the total weight of the composition.

21. The composition according to claim 1, wherein the pH of the composition ranges from 3 to 12.

22. The composition according to claim 21, wherein the pH of the composition ranges from 7 to 11.

23. A method for dyeing keratinous fibers, comprising:
applying to said fibers, in the presence of at least one oxidizing agent, a composition comprising, in a medium appropriate for dyeing, at least one oxidation base, at least one coupler, at least one aminated silicone, and monoethanolamine, wherein the at least one aminated silicone has a weight-average molecular weight ($M_w$) of greater than or equal to 75,000 g/mol, and wherein mixing the composition with a composition comprising at least one oxidizing agent results in a ready-to-use composition containing monoethanolamine in an amount ranging from 1 to 10% by weight, relative to the total weight of the ready-to-use composition; and
leaving said composition on said fibers for a time sufficient to develop the desired coloring effect.

24. The method according to claim 23, wherein the at least one oxidizing agent is chosen from hydrogen peroxide, urea hydrogen peroxide, alkali metal bromates and ferricyanides, persalts, oxidoreduction enzymes, and oxidoreduction enzymes with their respective donor or cofactor.

25. The method according to claim 24, wherein the at least one oxidizing agent is hydrogen peroxide.

26. A multicompartment device, comprising:
at least one first compartment comprising a composition comprising, in a medium appropriate for dyeing, at least one oxidation base, at least one coupler, at least one aminated silicone, and monoethanolamine, wherein the at least one aminated silicone has a weight-average molecular weight ($M_w$) of greater than or equal to 75,000 g/mol, and
at least one second compartment comprising a composition comprising, in a medium appropriate for dyeing, at least one oxidizing agent,
wherein mixing the composition of the first compartment with the composition of the second compartment results in a ready-to-use composition containing monoethanolamine in an amount ranging from 1 to 10% by weight, relative to the total weight of the ready-to-use composition.

27. A composition for dyeing keratinous fibers comprising, in a medium appropriate for dyeing:
at least one oxidation base,
at least one coupler,
at least one oxidizing agent,
at least one aminated silicone, and
monoethanolamine,
wherein the weight-average molecular weight ($M_w$) of the at least one aminated silicone is greater than or equal to 75,000 g/mol, and the monoethanolamine is present in an amount ranging from 1 to 10% by weight, relative to the total weight of the composition.

* * * * *